United States Patent
Izuhara et al.

(10) Patent No.: US 8,420,310 B2
(45) Date of Patent: Apr. 16, 2013

(54) METHOD FOR DETECTION OF IDIOPATHIC INTERSTITIAL PNEUMONIA

(75) Inventors: Kenji Izuhara, Saga (JP); Shoichiro Ohta, Saga (JP); Hiroshi Shiraishi, Saga (JP); Hisamichi Aizawa, Kurume (JP); Tomoaki Hoshino, Kurume (JP); Masaki Okamoto, Kurume (JP)

(73) Assignees: Saga University, Saga-Shi (JP); Kurume University, Kurume-Shi (JP)

( * ) Notice: Subject to any disclaimer, the term of this patent is extended or adjusted under 35 U.S.C. 154(b) by 0 days.

(21) Appl. No.: 12/995,769

(22) PCT Filed: Jun. 3, 2009

(86) PCT No.: PCT/JP2009/060567
§ 371 (c)(1),
(2), (4) Date: Dec. 2, 2010

(87) PCT Pub. No.: WO2009/148184
PCT Pub. Date: Dec. 10, 2009

(65) Prior Publication Data
US 2011/0086360 A1    Apr. 14, 2011

(30) Foreign Application Priority Data
Jun. 5, 2008   (JP) .................... 2008-147822

(51) Int. Cl.
*C12Q 1/68* (2006.01)
*G01N 33/48* (2006.01)
*G01N 33/50* (2006.01)
*G01N 33/53* (2006.01)

(52) U.S. Cl.
USPC ............. 435/4; 435/6.1; 435/7.1; 436/501

(58) Field of Classification Search .............. None
See application file for complete search history.

(56) References Cited

U.S. PATENT DOCUMENTS
2005/0095242 A1    5/2005 Ueda et al.

FOREIGN PATENT DOCUMENTS

| EP | 1 978 034 A1 | 10/2008 |
|---|---|---|
| JP | 2004-313133 A | 11/2004 |
| JP | 2005-500059 A | 1/2005 |
| WO | WO 02/052006 A1 | 7/2002 |
| WO | WO 03/016471 A2 | 2/2003 |
| WO | WO 03/072134 A1 | 9/2003 |
| WO | WO 2007/077934 A1 | 7/2007 |

OTHER PUBLICATIONS

: Lindner et al ( Arteriosclerosis, Thrombosis and vascular biology (2005) vol. 25, pp. 77-83.*
Pattison et al., 2010, Genome Medicine 2(88):1-6.*
Richter et al., 2005, Journal of Heredity 96(7):764-765.*
International Search Report, dated Aug. 25, 2009, issued in PCT/JP2009/060567.

(Continued)

*Primary Examiner* — Elizabeth C Kemmerer
(74) *Attorney, Agent, or Firm* — Birch, Stewart, Kolasch & Birch, LLP

(57) ABSTRACT

The present invention provides a method for detecting idiopathic interstitial pneumonia, which comprises measuring the expression level of a periostin gene or the amount of a periostin protein in a biological sample. Thereby, a method for detecting idiopathic interstitial pneumonia using a marker is provided.

8 Claims, 2 Drawing Sheets
(1 of 2 Drawing Sheet(s) Filed in Color)

OTHER PUBLICATIONS

Takayama, Go et al. "Periostin: A novel component of subepithelial fibrosis of bronchial asthma downstream of IL-4 and IL-13 signals", J. Allergy Clin Immunol, vol. 118, No. 1. pp. 98-104, Jul. 2006.

European Search Report issued on Feb. 2, 2012 in corresponding European Application No. 09758451.0.

Okamoto M. et al, "Periostin, a matrix protein, is a novel biomarker for idiopathic interstitial pneumonias", Database Biosis [online], Biosciences Information Service, Philadelphia Pa, May 2011.

* cited by examiner

```
SEQUENCE LISTING

<160> NUMBER OF SEQ ID NOS: 7

<210> SEQ ID NO 1
<211> LENGTH: 3213
<212> TYPE: DNA
<213> ORGANISM: Homo sapiens
<220> FEATURE:
<221> NAME/KEY: CDS
<222> LOCATION: (12)..(2522)

<400> SEQUENCE: 1
agagactcaa g atg att ccc ttt tta ccc atg ttt tct cta cta ttg ctg        50
            Met Ile Pro Phe Leu Pro Met Phe Ser Leu Leu Leu Leu
            1               5                   10 ctt att gtt aac cct ata aac gcc aac aat cat tat gac aag atc ttg        98
Leu Ile Val Asn Pro Ile Asn Ala Asn Asn His Tyr Asp Lys Ile Leu
    15                  20                  25 gct cat agt cgt atc agg ggt cgg gac caa ggc cca aat gtc tgt gcc       146
Ala His Ser Arg Ile Arg Gly Arg Asp Gln Gly Pro Asn Val Cys Ala
30                  35                  40                  45 ctt caa cag att ttg ggc acc aaa aag aaa tac ttc agc act tgt aag       194
Leu Gln Gln Ile Leu Gly Thr Lys Lys Lys Tyr Phe Ser Thr Cys Lys
```

```
                      50                  55                  60
aac tgg tat aaa aag tcc atc tgt gga cag aaa acg act gtt tta tat      242
Asn Trp Tyr Lys Lys Ser Ile Cys Gly Gln Lys Thr Thr Val Leu Tyr
             65                  70                  75 gaa tgt tgc cct ggt tat atg aga atg gaa gga atg aaa ggc tgc cca      290
Glu Cys Cys Pro Gly Tyr Met Arg Met Glu Gly Met Lys Gly Cys Pro
         80                  85                  90 gca gtt ttg ccc att gac cat gtt tat ggc act ctg ggc atc gtg gga      338
Ala Val Leu Pro Ile Asp His Val Tyr Gly Thr Leu Gly Ile Val Gly
     95                  100                 105 gcc acc aca acg cag cgc tat tct gac gcc tca aaa ctg agg gag gag      386
Ala Thr Thr Thr Gln Arg Tyr Ser Asp Ala Ser Lys Leu Arg Glu Glu
110                 115                 120                 125 atc gag gga aag gga tcc ttc act tac ttt gca ccg agt aat gag gct      434
Ile Glu Gly Lys Gly Ser Phe Thr Tyr Phe Ala Pro Ser Asn Glu Ala
                 130                 135                 140 tgg gac aac ttg gat tct gat atc cgt aga ggt ttg gag agc aac gtg      482
Trp Asp Asn Leu Asp Ser Asp Ile Arg Arg Gly Leu Glu Ser Asn Val
             145                 150                 155 aat gtt gaa tta ctg aat gct tta cat agt cac atg att aat aag aga      530
Asn Val Glu Leu Leu Asn Ala Leu His Ser His Met Ile Asn Lys Arg
         160                 165                 170 atg ttg acc aag gac tta aaa aat ggc atg att att cct tca atg tat      578
Met Leu Thr Lys Asp Leu Lys Asn Gly Met Ile Ile Pro Ser Met Tyr
     175                 180                 185 aac aat ttg ggg ctt ttc att aac cat tat cct aat ggg gtt gtc act      626
Asn Asn Leu Gly Leu Phe Ile Asn His Tyr Pro Asn Gly Val Val Thr
190                 195                 200                 205 gtt aat tgt gct cga atc atc cat ggg aac cag att gca aca aat ggt      674
Val Asn Cys Ala Arg Ile Ile His Gly Asn Gln Ile Ala Thr Asn Gly
                 210                 215                 220 gtt gtc cat gtc att gac cgt gtg ctt aca caa att ggt acc tca att      722
Val Val His Val Ile Asp Arg Val Leu Thr Gln Ile Gly Thr Ser Ile
             225                 230                 235 caa gac ttc att gaa gca gaa gat gac ctt tca tct ttt aga gca gct      770
Gln Asp Phe Ile Glu Ala Glu Asp Asp Leu Ser Ser Phe Arg Ala Ala
         240                 245                 250 gcc atc aca tcg gac ata ttg gag gcc ctt gga aga gac ggt cac ttc      818
Ala Ile Thr Ser Asp Ile Leu Glu Ala Leu Gly Arg Asp Gly His Phe
     255                 260                 265 aca ctc ttt gct ccc acc aat gag gct ttt gag aaa ctt cca cga ggt      866
Thr Leu Phe Ala Pro Thr Asn Glu Ala Phe Glu Lys Leu Pro Arg Gly
270                 275                 280                 285 gtc cta gaa agg ttc atg gga gac aaa gtg gct tcc gaa gct ctt atg      914
Val Leu Glu Arg Phe Met Gly Asp Lys Val Ala Ser Glu Ala Leu Met
                 290                 295                 300 aag tac cac atc tta aat act ctc cag tgt tct gag tct att atg gga      962
Lys Tyr His Ile Leu Asn Thr Leu Gln Cys Ser Glu Ser Ile Met Gly
             305                 310                 315 gga gca gtc ttt gag acg ctg gaa gga aat aca att gag ata gga tgt     1010
Gly Ala Val Phe Glu Thr Leu Glu Gly Asn Thr Ile Glu Ile Gly Cys
         320                 325                 330 gac ggt gac agt ata aca gta aat gga atc aaa atg gtg aac aaa aag     1058
Asp Gly Asp Ser Ile Thr Val Asn Gly Ile Lys Met Val Asn Lys Lys
     335                 340                 345 gat att gtg aca aat aat ggt gtg atc cat ttg att gat cag gtc cta     1106
Asp Ile Val Thr Asn Asn Gly Val Ile His Leu Ile Asp Gln Val Leu
350                 355                 360                 365 att cct gat tct gcc aaa caa gtt att gag ctg gct gga aaa cag caa     1154
Ile Pro Asp Ser Ala Lys Gln Val Ile Glu Leu Ala Gly Lys Gln Gln
```

```
                  370                 375                 380
acc acc ttc acg gat ctt gtg gcc caa tta ggc ttg gca tct gct ctg   1202
Thr Thr Phe Thr Asp Leu Val Ala Gln Leu Gly Leu Ala Ser Ala Leu
            385                 390                 395 agg cca gat gga gaa tac act ttg ctg gca cct gtg aat aat gca ttt   1250
Arg Pro Asp Gly Glu Tyr Thr Leu Leu Ala Pro Val Asn Asn Ala Phe
        400                 405                 410 tct gat gat act ctc agc atg gtt cag cgc ctc ctt aaa tta att ctg   1298
Ser Asp Asp Thr Leu Ser Met Val Gln Arg Leu Leu Lys Leu Ile Leu
    415                 420                 425 cag aat cac ata ttg aaa gta aaa gtt ggc ctt aat gag ctt tac aac   1346
Gln Asn His Ile Leu Lys Val Lys Val Gly Leu Asn Glu Leu Tyr Asn
430                 435                 440                 445 ggg caa ata ctg gaa acc atc gga ggc aaa cag ctc aga gtc ttc gta   1394
Gly Gln Ile Leu Glu Thr Ile Gly Gly Lys Gln Leu Arg Val Phe Val
                450                 455                 460 tat cgt aca gct gtc tgc att gaa aat tca tgc atg gag aaa ggg agt   1442
Tyr Arg Thr Ala Val Cys Ile Glu Asn Ser Cys Met Glu Lys Gly Ser
            465                 470                 475 aag caa ggg aga aac ggt gcg att cac ata ttc cgc gag atc atc aag   1490
Lys Gln Gly Arg Asn Gly Ala Ile His Ile Phe Arg Glu Ile Ile Lys
        480                 485                 490 cca gca gag aaa tcc ctc cat gaa aag tta aaa caa gat aag cgc ttt   1538
Pro Ala Glu Lys Ser Leu His Glu Lys Leu Lys Gln Asp Lys Arg Phe
    495                 500                 505 agc acc ttc ctc agc cta ctt gaa gct gca gac ttg aaa gag ctc ctg   1586
Ser Thr Phe Leu Ser Leu Leu Glu Ala Ala Asp Leu Lys Glu Leu Leu
510                 515                 520                 525 aca caa cct gga gac tgg aca tta ttt gtg cca acc aat gat gct ttt   1634
Thr Gln Pro Gly Asp Trp Thr Leu Phe Val Pro Thr Asn Asp Ala Phe
                530                 535                 540 aag gga atg act agt gaa gaa aaa gaa att ctg ata cgg gac aaa aat   1682
Lys Gly Met Thr Ser Glu Glu Lys Glu Ile Leu Ile Arg Asp Lys Asn
            545                 550                 555 gct ctt caa aac atc att ctt tat cac ctg aca cca gga gtt ttc att   1730
Ala Leu Gln Asn Ile Ile Leu Tyr His Leu Thr Pro Gly Val Phe Ile
        560                 565                 570 gga aaa gga ttt gaa cct ggt gtt act aac att tta aag acc aca caa   1778
Gly Lys Gly Phe Glu Pro Gly Val Thr Asn Ile Leu Lys Thr Thr Gln
    575                 580                 585 gga agc aaa atc ttt ctg aaa gaa gta aat gat aca ctt ctg gtg aat   1826
Gly Ser Lys Ile Phe Leu Lys Glu Val Asn Asp Thr Leu Leu Val Asn
590                 595                 600                 605 gaa ttg aaa tca aaa gaa tct gac atc atg aca aca aat ggt gta att   1874
Glu Leu Lys Ser Lys Glu Ser Asp Ile Met Thr Thr Asn Gly Val Ile
                610                 615                 620 cat gtt gta gat aaa ctc ctc tat cca gca gac aca cct gtt gga aat   1922
His Val Val Asp Lys Leu Leu Tyr Pro Ala Asp Thr Pro Val Gly Asn
            625                 630                 635 gat caa ctg ctg gaa ata ctt aat aaa tta atc aaa tac atc caa att   1970
Asp Gln Leu Leu Glu Ile Leu Asn Lys Leu Ile Lys Tyr Ile Gln Ile
        640                 645                 650 aag ttt gtt cgt ggt agc acc ttc aaa gaa atc ccc gtg act gtc tat   2018
Lys Phe Val Arg Gly Ser Thr Phe Lys Glu Ile Pro Val Thr Val Tyr
    655                 660                 665 aca act aaa att ata acc aaa gtt gtg gaa cca aaa att aaa gtg att   2066
Thr Thr Lys Ile Ile Thr Lys Val Val Glu Pro Lys Ile Lys Val Ile
670                 675                 680                 685 gaa ggc agt ctt cag cct att atc aaa act gaa gga ccc aca cta aca   2114
Glu Gly Ser Leu Gln Pro Ile Ile Lys Thr Glu Gly Pro Thr Leu Thr
```

```
                690                 695                 700
aaa gtc aaa att gaa ggt gaa cct gaa ttc aga ctg att aaa gaa ggt    2162
Lys Val Lys Ile Glu Gly Glu Pro Glu Phe Arg Leu Ile Lys Glu Gly
            705                 710                 715 gaa aca ata act gaa gtg atc cat gga gag cca att att aaa aaa tac    2210
Glu Thr Ile Thr Glu Val Ile His Gly Glu Pro Ile Ile Lys Lys Tyr
        720                 725                 730 acc aaa atc att gat gga gtg cct gtg gaa ata act gaa aaa gag aca    2258
Thr Lys Ile Ile Asp Gly Val Pro Val Glu Ile Thr Glu Lys Glu Thr
    735                 740                 745 cga gaa gaa cga atc att aca ggt cct gaa ata aaa tac act agg att    2306
Arg Glu Glu Arg Ile Ile Thr Gly Pro Glu Ile Lys Tyr Thr Arg Ile
750                 755                 760                 765 tct act gga ggt gga gaa aca gaa gaa act ctg aag aaa ttg tta caa    2354
Ser Thr Gly Gly Gly Glu Thr Glu Glu Thr Leu Lys Lys Leu Leu Gln
                770                 775                 780 gaa gag gtc acc aag gtc acc aaa ttc att gaa ggt ggt gat ggt cat    2402
Glu Glu Val Thr Lys Val Thr Lys Phe Ile Glu Gly Gly Asp Gly His
            785                 790                 795 tta ttt gaa gat gaa gaa att aaa aga ctg ctt cag gga gac aca ccc    2450
Leu Phe Glu Asp Glu Glu Ile Lys Arg Leu Leu Gln Gly Asp Thr Pro
        800                 805                 810 gtg agg aag ttg caa gcc aac aaa aaa gtt caa ggt tct aga aga cga    2498
Val Arg Lys Leu Gln Ala Asn Lys Lys Val Gln Gly Ser Arg Arg Arg
    815                 820                 825 tta agg gaa ggt cgt tct cag tga aaatccaaaa accagaaaaa aatgtttata    2552
Leu Arg Glu Gly Arg Ser Gln
830                 835 caaccctaag tcataaccct gaccttagaa aattgtgaga gccaagttga cttcaggaac    2612
tgaaacatca gcacaaagaa gcaatcatca aataattctg aacacaaatt taatattttt    2672
ttttctgaat gagaaacatg agggaaattg tggagttagc ctcctgtggt aaaggaattg    2732
aagaaaatat aacaccttac acccttttc atcttgacat taaaagttct ggctaacttt    2792
ggaatccatt agagaaaaat ccttgtcacc agattcatta caattcaaat cgaagagttg    2852
tgaactgtta tcccattgaa aagaccgagc cttgtatgta tgttatggat acataaaatg    2912
cacgcaagcc attatctctc catgggaagc taagttataa aaataggtgc ttggtgtaca    2972
aaacttttta tatcaaaagg ctttgcacat ttctatatga gtgggtttac tggtaaatta    3032
tgttattttt tacaactaat tttgtactct cagaatgttt gtcatatgct tcttgcaatg    3092
catatttttt aatctcaaac gtttcaataa aaccattttt cagatataaa gagaattact    3152
tcaaattgag taattcagaa aaactcaaga tttaagttaa aaagtggttt ggacttggga    3212
a                                                                   3213
```

<210> SEQ ID NO 2
<211> LENGTH: 836
<212> TYPE: PRT
<213> ORGANISM: Homo sapiens

<400> SEQUENCE: 2

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr

-continued

```
            50                  55                  60
Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Phe Met Gly Asp Lys Val Ala Ser Glu Ala Leu Met Lys Tyr His
290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Val Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480
```

```
Arg Asn Gly Ala Ile His Ile Phe Arg Glu Ile Ile Lys Pro Ala Glu
            485                 490                 495

Lys Ser Leu His Glu Lys Leu Lys Gln Asp Lys Arg Phe Ser Thr Phe
        500                 505                 510

Leu Ser Leu Leu Glu Ala Ala Asp Leu Lys Glu Leu Leu Thr Gln Pro
    515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
        675                 680                 685

Leu Gln Pro Ile Ile Lys Thr Glu Gly Pro Thr Leu Thr Lys Val Lys
    690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
        755                 760                 765

Gly Gly Glu Thr Glu Glu Thr Leu Lys Lys Leu Leu Gln Glu Glu Val
    770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gln Gly Ser Arg Arg Arg Leu Arg Glu
            820                 825                 830

Gly Arg Ser Gln
        835

<210> SEQ ID NO 3
<211> LENGTH: 2958
<212> TYPE: DNA
<213> ORGANISM: Homo sapiens
<220> FEATURE:
<221> NAME/KEY: CDS
<222> LOCATION: (12)..(2267)

<400> SEQUENCE: 3
```

-continued

| | |
|---|---|
| agagactcaa g atg att ccc ttt tta ccc atg ttt tct cta cta ttg ctg<br>           Met Ile Pro Phe Leu Pro Met Phe Ser Leu Leu Leu Leu<br>            1              5                  10 | 50 |
| ctt att gtt aac cct ata aac gcc aac aat cat tat gac aag atc ttg<br>Leu Ile Val Asn Pro Ile Asn Ala Asn Asn His Tyr Asp Lys Ile Leu<br> 15                   20                   25 | 98 |
| gct cat agt cgt atc agg ggt cgg gac caa ggc cca aat gtc tgt gcc<br>Ala His Ser Arg Ile Arg Gly Arg Asp Gln Gly Pro Asn Val Cys Ala<br>30                35                  40              45 | 146 |
| ctt caa cag att ttg ggc acc aaa aag aaa tac ttc agc act tgt aag<br>Leu Gln Gln Ile Leu Gly Thr Lys Lys Lys Tyr Phe Ser Thr Cys Lys<br>           50                  55                  60 | 194 |
| aac tgg tat aaa aag tcc atc tgt gga cag aaa acg act gtt tta tat<br>Asn Trp Tyr Lys Lys Ser Ile Cys Gly Gln Lys Thr Thr Val Leu Tyr<br>     65                  70                  75 | 242 |
| gaa tgt tgc cct ggt tat atg aga atg gaa gga atg aaa ggc tgc cca<br>Glu Cys Cys Pro Gly Tyr Met Arg Met Glu Gly Met Lys Gly Cys Pro<br>           80                  85              90 | 290 |
| gca gtt ttg ccc att gac cat gtt tat ggc act ctg ggc atc gtg gga<br>Ala Val Leu Pro Ile Asp His Val Tyr Gly Thr Leu Gly Ile Val Gly<br>     95                 100               105 | 338 |
| gcc acc aca acg cag cgc tat tct gac gcc tca aaa ctg agg gag gag<br>Ala Thr Thr Thr Gln Arg Tyr Ser Asp Ala Ser Lys Leu Arg Glu Glu<br>110                115                 120             125 | 386 |
| atc gag gga aag gga tcc ttc act tac ttt gca ccg agt aat gag gct<br>Ile Glu Gly Lys Gly Ser Phe Thr Tyr Phe Ala Pro Ser Asn Glu Ala<br>             130                 135             140 | 434 |
| tgg gac aac ttg gat tct gat atc cgt aga ggt ttg gag agc aac gtg<br>Trp Asp Asn Leu Asp Ser Asp Ile Arg Arg Gly Leu Glu Ser Asn Val<br>                145                 150             155 | 482 |
| aat gtt gaa tta ctg aat gct tta cat agt cac atg att aat aag aga<br>Asn Val Glu Leu Leu Asn Ala Leu His Ser His Met Ile Asn Lys Arg<br>         160                 165               170 | 530 |
| atg ttg acc aag gac tta aaa aat ggc atg att att cct tca atg tat<br>Met Leu Thr Lys Asp Leu Lys Asn Gly Met Ile Ile Pro Ser Met Tyr<br>175                180                 185 | 578 |
| aac aat ttg ggg ctt ttc att aac cat tat cct aat ggg gtt gtc act<br>Asn Asn Leu Gly Leu Phe Ile Asn His Tyr Pro Asn Gly Val Val Thr<br>      190               195               200             205 | 626 |
| gtt aat tgt gct cga atc atc cat ggg aac cag att gca aca aat ggt<br>Val Asn Cys Ala Arg Ile Ile His Gly Asn Gln Ile Ala Thr Asn Gly<br>                210                 215             220 | 674 |
| gtt gtc cat gtc att gac cgt gtg ctt aca caa att ggt acc tca att<br>Val Val His Val Ile Asp Arg Val Leu Thr Gln Ile Gly Thr Ser Ile<br>         225                 230               235 | 722 |
| caa gac ttc att gaa gca gaa gat gac ctt tca tct ttt aga gca gct<br>Gln Asp Phe Ile Glu Ala Glu Asp Asp Leu Ser Ser Phe Arg Ala Ala<br>             240                 245             250 | 770 |
| gcc atc aca tcg gac ata ttg gag gcc ctt gga aga gac ggt cac ttc<br>Ala Ile Thr Ser Asp Ile Leu Glu Ala Leu Gly Arg Asp Gly His Phe<br>255                260                 265 | 818 |
| aca ctc ttt gct ccc acc aat gag gct ttt gag aaa ctt cca cga ggt<br>Thr Leu Phe Ala Pro Thr Asn Glu Ala Phe Glu Lys Leu Pro Arg Gly<br>270                275                 280             285 | 866 |
| gtc cta gaa agg ttc atg gga gac aaa gtg gct tcc gaa gct ctt atg<br>Val Leu Glu Arg Phe Met Gly Asp Lys Val Ala Ser Glu Ala Leu Met<br>             290                 295             300 | 914 |
| aag tac cac atc tta aat act ctc cag tgt tct gag tct att atg gga<br>Lys Tyr His Ile Leu Asn Thr Leu Gln Cys Ser Glu Ser Ile Met Gly<br>         305                 310               315 | 962 |

```
                                                           -continued
gga gca gtc ttt gag acg ctg gaa gga aat aca att gag ata gga tgt   1010
Gly Ala Val Phe Glu Thr Leu Glu Gly Asn Thr Ile Glu Ile Gly Cys
        320                 325                 330 gac ggt gac agt ata aca gta aat gga atc aaa atg gtg aac aaa aag   1058
Asp Gly Asp Ser Ile Thr Val Asn Gly Ile Lys Met Val Asn Lys Lys
335                 340                 345 gat att gtg aca aat aat ggt gtg atc cat ttg att gat cag gtc cta   1106
Asp Ile Val Thr Asn Asn Gly Val Ile His Leu Ile Asp Gln Val Leu
350                 355                 360                 365 att cct gat tct gcc aaa caa gtt att gag ctg gct gga aaa cag caa   1154
Ile Pro Asp Ser Ala Lys Gln Val Ile Glu Leu Ala Gly Lys Gln Gln
                370                 375                 380 acc acc ttc acg gat ctt gtg gcc caa tta ggc ttg gca tct gct ctg   1202
Thr Thr Phe Thr Asp Leu Val Ala Gln Leu Gly Leu Ala Ser Ala Leu
        385                 390                 395 agg cca gat gga gaa tac act ttg ctg gca cct gtg aat aat gca ttt   1250
Arg Pro Asp Gly Glu Tyr Thr Leu Leu Ala Pro Val Asn Asn Ala Phe
400                 405                 410 tct gat gat act ctc agc atg gtt cag cgc ctc ctt aaa tta att ctg   1298
Ser Asp Asp Thr Leu Ser Met Val Gln Arg Leu Leu Lys Leu Ile Leu
415                 420                 425 cag aat cac ata ttg aaa gta aaa gtt ggc ctt aat gag ctt tac aac   1346
Gln Asn His Ile Leu Lys Val Lys Val Gly Leu Asn Glu Leu Tyr Asn
430                 435                 440                 445 ggg caa ata ctg gaa acc atc gga ggc aaa cag ctc aga gtc ttc gta   1394
Gly Gln Ile Leu Glu Thr Ile Gly Gly Lys Gln Leu Arg Val Phe Val
                450                 455                 460 tat cgt aca gct gtc tgc att gaa aat tca tgc atg gag aaa ggg agt   1442
Tyr Arg Thr Ala Val Cys Ile Glu Asn Ser Cys Met Glu Lys Gly Ser
        465                 470                 475 aag caa ggg aga aac ggt gcg att cac ata ttc cgc gag atc atc aag   1490
Lys Gln Gly Arg Asn Gly Ala Ile His Ile Phe Arg Glu Ile Ile Lys
480                 485                 490 cca gca gag aaa tcc ctc cat gaa aag tta aaa caa gat aag cgc ttt   1538
Pro Ala Glu Lys Ser Leu His Glu Lys Leu Lys Gln Asp Lys Arg Phe
495                 500                 505 agc acc ttc ctc agc cta ctt gaa gct gca gac ttg aaa gag ctc ctg   1586
Ser Thr Phe Leu Ser Leu Leu Glu Ala Ala Asp Leu Lys Glu Leu Leu
510                 515                 520                 525 aca caa cct gga gac tgg aca tta ttt gtg cca acc aat gat gct ttt   1634
Thr Gln Pro Gly Asp Trp Thr Leu Phe Val Pro Thr Asn Asp Ala Phe
                530                 535                 540 aag gga atg act agt gaa gaa aaa gaa att ctg ata cgg gac aaa aat   1682
Lys Gly Met Thr Ser Glu Glu Lys Glu Ile Leu Ile Arg Asp Lys Asn
        545                 550                 555 gct ctt caa aac atc att ctt tat cac ctg aca cca gga gtt ttc att   1730
Ala Leu Gln Asn Ile Ile Leu Tyr His Leu Thr Pro Gly Val Phe Ile
560                 565                 570 gga aaa gga ttt gaa cct ggt gtt act aac att tta aag acc aca caa   1778
Gly Lys Gly Phe Glu Pro Gly Val Thr Asn Ile Leu Lys Thr Thr Gln
575                 580                 585 gga agc aaa atc ttt ctg aaa gaa gta aat gat aca ctt ctg gtg aat   1826
Gly Ser Lys Ile Phe Leu Lys Glu Val Asn Asp Thr Leu Leu Val Asn
590                 595                 600                 605 gaa ttg aaa tca aaa gaa tct gac atc atg aca aca aat ggt gta att   1874
Glu Leu Lys Ser Lys Glu Ser Asp Ile Met Thr Thr Asn Gly Val Ile
                610                 615                 620 cat gtt gta gat aaa ctc ctc tat cca gca gac aca cct gtt gga aat   1922
His Val Val Asp Lys Leu Leu Tyr Pro Ala Asp Thr Pro Val Gly Asn
        625                 630                 635
```

-continued

| | | |
|---|---|---|
| gat caa ctg ctg gaa ata ctt aat aaa tta atc aaa tac atc caa att<br>Asp Gln Leu Leu Glu Ile Leu Asn Lys Leu Ile Lys Tyr Ile Gln Ile<br>640　　　　　　　645　　　　　　　650 | | 1970 |
| aag ttt gtt cgt ggt agc acc ttc aaa gaa atc ccc gtg act gtc tat<br>Lys Phe Val Arg Gly Ser Thr Phe Lys Glu Ile Pro Val Thr Val Tyr<br>655　　　　　　　660　　　　　　　665 | | 2018 |
| aag cca att att aaa aaa tac acc aaa atc att gat gga gtg cct gtg<br>Lys Pro Ile Ile Lys Lys Tyr Thr Lys Ile Ile Asp Gly Val Pro Val<br>670　　　　　　　675　　　　　　　680　　　　　　　685 | | 2066 |
| gaa ata act gaa aaa gag aca cga gaa gaa cga atc att aca ggt cct<br>Glu Ile Thr Glu Lys Glu Thr Arg Glu Glu Arg Ile Ile Thr Gly Pro<br>　　　　　　　690　　　　　　　695　　　　　　　700 | | 2114 |
| gaa ata aaa tac act agg att tct act gga ggt gga gaa aca gaa gaa<br>Glu Ile Lys Tyr Thr Arg Ile Ser Thr Gly Gly Gly Glu Thr Glu Glu<br>705　　　　　　　710　　　　　　　715 | | 2162 |
| act ctg aag aaa ttg tta caa gaa gac aca ccc gtg agg aag ttg caa<br>Thr Leu Lys Lys Leu Leu Gln Glu Asp Thr Pro Val Arg Lys Leu Gln<br>720　　　　　　　725　　　　　　　730 | | 2210 |
| gcc aac aaa aaa gtt caa ggt tct aga aga cga tta agg gaa ggt cgt<br>Ala Asn Lys Lys Val Gln Gly Ser Arg Arg Arg Leu Arg Glu Gly Arg<br>735　　　　　　　740　　　　　　　745 | | 2258 |
| tct cag tga aaatccaaaa accagaaaaa aatgtttata caaccctaag<br>Ser Gln<br>750 | | 2307 |
| tcaataacct gaccttagaa aattgtgaga gccaagttga cttcaggaac tgaaacatca | | 2367 |
| gcacaaagaa gcaatcatca aataattctg aacacaaatt taatattttt ttttctgaat | | 2427 |
| gagaaacatg agggaaattg tggagttagc ctcctgtggt aaaggaattg aagaaaatat | | 2487 |
| aacaccttac acccttttc atcttgacat taaaagttct ggctaacttt ggaatccatt | | 2547 |
| agagaaaaat ccttgtcacc agattcatta caattcaaat cgaagagttg tgaactgtta | | 2607 |
| tcccattgaa aagaccgagc cttgtatgta tgttatggat acataaaatg cacgcaagcc | | 2667 |
| attatctctc catgggaagc taagttataa aaataggtgc ttggtgtaca aaacttttta | | 2727 |
| tatcaaaagg cttttgcacat ttctatatga gtgggtttac tggtaaatta tgttattttt | | 2787 |
| tacaactaat tttgtactct cagaatgttt gtcatatgct tcttgcaatg catattttt | | 2847 |
| aatctcaaac gtttcaataa aaccattttt cagatataaa gagaattact tcaaattgag | | 2907 |
| taattcagaa aaactcaaga tttaagttaa aaagtggttt ggacttggga a | | 2958 |

<210> SEQ ID NO 4
<211> LENGTH: 751
<212> TYPE: PRT
<213> ORGANISM: Homo sapiens

<400> SEQUENCE: 4

Met Ile Pro Phe Leu Pro Met Phe Ser Leu Leu Leu Leu Leu Ile Val
1　　　　　　　5　　　　　　　10　　　　　　　15

Asn Pro Ile Asn Ala Asn Asn His Tyr Asp Lys Ile Leu Ala His Ser
　　　　　20　　　　　　　25　　　　　　　30

Arg Ile Arg Gly Arg Asp Gln Gly Pro Asn Val Cys Ala Leu Gln Gln
　　35　　　　　　　40　　　　　　　45

Ile Leu Gly Thr Lys Lys Lys Tyr Phe Ser Thr Cys Lys Asn Trp Tyr
50　　　　　　　55　　　　　　　60

Lys Lys Ser Ile Cys Gly Gln Lys Thr Thr Val Leu Tyr Glu Cys Cys
65　　　　　　　70　　　　　　　75　　　　　　　80

Pro Gly Tyr Met Arg Met Glu Gly Met Lys Gly Cys Pro Ala Val Leu
　　　　　85　　　　　　　90　　　　　　　95

```
Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
            195                 200                 205

Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
            275                 280                 285

Arg Phe Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Val Gln Arg Leu Leu Lys Leu Ile Leu Gln Asn His
            420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
            450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
            515                 520                 525
```

```
Gly Asp Trp Thr Leu Phe Val Pro Thr Asn Asp Ala Phe Lys Gly Met
        530                 535                 540
Thr Ser Glu Glu Lys Glu Ile Leu Ile Arg Asp Lys Asn Ala Leu Gln
545                 550                 555                 560
Asn Ile Ile Leu Tyr His Leu Thr Pro Gly Val Phe Ile Gly Lys Gly
                565                 570                 575
Phe Glu Pro Gly Val Thr Asn Ile Leu Lys Thr Thr Gln Gly Ser Lys
            580                 585                 590
Ile Phe Leu Lys Glu Val Asn Asp Thr Leu Leu Val Asn Glu Leu Lys
        595                 600                 605
Ser Lys Glu Ser Asp Ile Met Thr Thr Asn Gly Val Ile His Val Val
610                 615                 620
Asp Lys Leu Leu Tyr Pro Ala Asp Thr Pro Val Gly Asn Asp Gln Leu
625                 630                 635                 640
Leu Glu Ile Leu Asn Lys Leu Ile Lys Tyr Ile Gln Ile Lys Phe Val
                645                 650                 655
Arg Gly Ser Thr Phe Lys Glu Ile Pro Val Thr Val Tyr Lys Pro Ile
            660                 665                 670
Ile Lys Lys Tyr Thr Lys Ile Ile Asp Gly Val Pro Val Glu Ile Thr
        675                 680                 685
Glu Lys Glu Thr Arg Glu Glu Arg Ile Ile Thr Gly Pro Glu Ile Lys
690                 695                 700
Tyr Thr Arg Ile Ser Thr Gly Gly Glu Thr Glu Glu Thr Leu Lys
705                 710                 715                 720
Lys Leu Leu Gln Glu Asp Thr Pro Val Arg Lys Leu Gln Ala Asn Lys
                725                 730                 735
Lys Val Gln Gly Ser Arg Arg Leu Arg Glu Gly Arg Ser Gln
            740                 745                 750

<210> SEQ ID NO 5
<211> LENGTH: 2360
<212> TYPE: DNA
<213> ORGANISM: Homo sapiens
<220> FEATURE:
<221> NAME/KEY: CDS
<222> LOCATION: (12)..(2360)

<400> SEQUENCE: 5
agagactcaa g atg att ccc ttt tta ccc atg ttt tct cta cta ttg ctg      50
            Met Ile Pro Phe Leu Pro Met Phe Ser Leu Leu Leu Leu
             1               5                  10 ctt att gtt aac cct ata aac gcc aac aat cat tat gac aag atc ttg      98
Leu Ile Val Asn Pro Ile Asn Ala Asn Asn His Tyr Asp Lys Ile Leu
 15                  20                  25 gct cat agt cgt atc agg ggt cgg gac caa ggc cca aat gtc tgt gcc     146
Ala His Ser Arg Ile Arg Gly Arg Asp Gln Gly Pro Asn Val Cys Ala
 30                  35                  40                  45 ctt caa cag att ttg ggc acc aaa aag aaa tac ttc agc act tgt aag     194
Leu Gln Gln Ile Leu Gly Thr Lys Lys Lys Tyr Phe Ser Thr Cys Lys
                 50                  55                  60 aac tgg tat aaa aag tcc atc tgt gga cag aaa acg act gtg tta tat     242
Asn Trp Tyr Lys Lys Ser Ile Cys Gly Gln Lys Thr Thr Val Leu Tyr
             65                  70                  75 gaa tgt tgc cct ggt tat atg aga atg gaa gga atg aaa ggc tgc cca     290
Glu Cys Cys Pro Gly Tyr Met Arg Met Glu Gly Met Lys Gly Cys Pro
         80                  85                  90 gca gtt ttg ccc att gac cat gtt tat ggc act ctg ggc atc gtg gga     338
Ala Val Leu Pro Ile Asp His Val Tyr Gly Thr Leu Gly Ile Val Gly
     95                 100                 105
```

```
                                   95                       100                       105
gcc acc aca acg cag cgc tat tct gac gcc tca aaa ctg agg gag gag       386
Ala Thr Thr Thr Gln Arg Tyr Ser Asp Ala Ser Lys Leu Arg Glu Glu
110                     115                     120                     125 atc gag gga aag gga tcc ttc act tac ttt gca ccg agt aat gag gct       434
Ile Glu Gly Lys Gly Ser Phe Thr Tyr Phe Ala Pro Ser Asn Glu Ala
                        130                     135                     140 tgg gac aac ttg gat tct gat atc cgt aga ggt ttg gag agc aac gtg       482
Trp Asp Asn Leu Asp Ser Asp Ile Arg Arg Gly Leu Glu Ser Asn Val
            145                     150                     155 aat gtt gaa tta ctg aat gct tta cat agt cac atg att aat aag aga       530
Asn Val Glu Leu Leu Asn Ala Leu His Ser His Met Ile Asn Lys Arg
160                     165                     170 atg ttg acc aag gac tta aaa aat ggc atg att att cct tca atg tat       578
Met Leu Thr Lys Asp Leu Lys Asn Gly Met Ile Ile Pro Ser Met Tyr
        175                     180                     185 aac aat ttg ggg ctt ttc att aac cat tat cct aat ggg gtt gtc act       626
Asn Asn Leu Gly Leu Phe Ile Asn His Tyr Pro Asn Gly Val Val Thr
190                     195                     200                     205 gtt aat tgt gct cga atc atc cat ggg aac cag att gca aca aat ggt       674
Val Asn Cys Ala Arg Ile Ile His Gly Asn Gln Ile Ala Thr Asn Gly
                        210                     215                     220 gtt gtc cat gtc att gac cgt gtg ctt aca caa att ggt acc tca att       722
Val Val His Val Ile Asp Arg Val Leu Thr Gln Ile Gly Thr Ser Ile
            225                     230                     235 caa gac ttc att gaa gca gaa gat gac ctt tca tct ttt aga gca gct       770
Gln Asp Phe Ile Glu Ala Glu Asp Asp Leu Ser Ser Phe Arg Ala Ala
240                     245                     250 gcc atc aca tcg gac ata ttg gag gcc ctt gga aga gac ggt cac ttc       818
Ala Ile Thr Ser Asp Ile Leu Glu Ala Leu Gly Arg Asp Gly His Phe
        255                     260                     265 aca ctc ttt gct ccc acc aat gag gct ttt gag aaa ctt cca cga ggt       866
Thr Leu Phe Ala Pro Thr Asn Glu Ala Phe Glu Lys Leu Pro Arg Gly
270                     275                     280                     285 gtc cta gaa agg atc atg gga gac aaa gtg gct tcc gaa gct ctt atg       914
Val Leu Glu Arg Ile Met Gly Asp Lys Val Ala Ser Glu Ala Leu Met
                        290                     295                     300 aag tac cac atc tta aat act ctc cag tgt tct gag tct att atg gga       962
Lys Tyr His Ile Leu Asn Thr Leu Gln Cys Ser Glu Ser Ile Met Gly
            305                     310                     315 gga gca gtc ttt gag acg ctg gaa gga aat aca att gag ata gga tgt      1010
Gly Ala Val Phe Glu Thr Leu Glu Gly Asn Thr Ile Glu Ile Gly Cys
        320                     325                     330 gac ggt gac agt ata aca gta aat gga atc aaa atg gtg aac aaa aag      1058
Asp Gly Asp Ser Ile Thr Val Asn Gly Ile Lys Met Val Asn Lys Lys
335                     340                     345 gat att gtg aca aat aat ggt gtg atc cat ttg att gat cag gtc cta      1106
Asp Ile Val Thr Asn Asn Gly Val Ile His Leu Ile Asp Gln Val Leu
350                     355                     360                     365 att cct gat tct gcc aaa caa gtt att gag ctg gct gga aaa cag caa      1154
Ile Pro Asp Ser Ala Lys Gln Val Ile Glu Leu Ala Gly Lys Gln Gln
                        370                     375                     380 acc acc ttc acg gat ctt gtg gcc caa tta ggc ttg gca tct gct ctg      1202
Thr Thr Phe Thr Asp Leu Val Ala Gln Leu Gly Leu Ala Ser Ala Leu
            385                     390                     395 agg cca gat gga gaa tac act ttg ctg gca cct gtg aat aat gca ttt      1250
Arg Pro Asp Gly Glu Tyr Thr Leu Leu Ala Pro Val Asn Asn Ala Phe
        400                     405                     410 tct gat gat act ctc agc atg gat cag cgc ctc ctt aaa tta att ctg      1298
Ser Asp Asp Thr Leu Ser Met Asp Gln Arg Leu Leu Lys Leu Ile Leu
```

```
                     415                 420                 425
cag aat cac ata ttg aaa gta aaa gtt ggc ctt aat gag ctt tac aac   1346
Gln Asn His Ile Leu Lys Val Lys Val Gly Leu Asn Glu Leu Tyr Asn
430                 435                 440                 445 ggg caa ata ctg gaa acc atc gga ggc aaa cag ctc aga gtc ttc gta   1394
Gly Gln Ile Leu Glu Thr Ile Gly Gly Lys Gln Leu Arg Val Phe Val
                450                 455                 460 tat cgt aca gct gtc tgc att gaa aat tca tgc atg gag aaa ggg agt   1442
Tyr Arg Thr Ala Val Cys Ile Glu Asn Ser Cys Met Glu Lys Gly Ser
                    465                 470                 475 aag caa ggg aga aac ggt gcg att cac ata ttc cgc gag atc atc aag   1490
Lys Gln Gly Arg Asn Gly Ala Ile His Ile Phe Arg Glu Ile Ile Lys
            480                 485                 490 cca gca gag aaa tcc ctc cat gaa aag tta aaa caa gat aag cgc ttt   1538
Pro Ala Glu Lys Ser Leu His Glu Lys Leu Lys Gln Asp Lys Arg Phe
        495                 500                 505 agc acc ttc ctc agc cta ctt gaa gct gca gac ttg aaa gag ctc ctg   1586
Ser Thr Phe Leu Ser Leu Leu Glu Ala Ala Asp Leu Lys Glu Leu Leu
510                 515                 520                 525 aca caa cct gga gac tgg aca tta ttt gtg cca acc aat gat gct ttt   1634
Thr Gln Pro Gly Asp Trp Thr Leu Phe Val Pro Thr Asn Asp Ala Phe
                530                 535                 540 aag gga atg act agt gaa gaa aaa gaa att ctg ata cgg gac aaa aat   1682
Lys Gly Met Thr Ser Glu Glu Lys Glu Ile Leu Ile Arg Asp Lys Asn
                    545                 550                 555 gct ctt caa aac atc att ctt tat cac ctg aca cca gga gtt ttc att   1730
Ala Leu Gln Asn Ile Ile Leu Tyr His Leu Thr Pro Gly Val Phe Ile
            560                 565                 570 gga aaa gga ttt gaa cct ggt gtt act aac att tta aag acc aca caa   1778
Gly Lys Gly Phe Glu Pro Gly Val Thr Asn Ile Leu Lys Thr Thr Gln
        575                 580                 585 gga agc aaa atc ttt ctg aaa gaa gta aat gat aca ctt ctg gtg aat   1826
Gly Ser Lys Ile Phe Leu Lys Glu Val Asn Asp Thr Leu Leu Val Asn
590                 595                 600                 605 gaa ttg aaa tca aaa gaa tct gac atc atg aca aca aat ggt gta att   1874
Glu Leu Lys Ser Lys Glu Ser Asp Ile Met Thr Thr Asn Gly Val Ile
                610                 615                 620 cat gtt gta gat aaa ctc ctc tat cca gca gac aca cct gtt gga aat   1922
His Val Val Asp Lys Leu Leu Tyr Pro Ala Asp Thr Pro Val Gly Asn
                    625                 630                 635 gat caa ctg ctg gaa ata ctt aat aaa tta atc aaa tac atc caa att   1970
Asp Gln Leu Leu Glu Ile Leu Asn Lys Leu Ile Lys Tyr Ile Gln Ile
            640                 645                 650 aag ttt gtt cgt ggt agc acc ttc aaa gaa atc ccc gtg act gtc tat   2018
Lys Phe Val Arg Gly Ser Thr Phe Lys Glu Ile Pro Val Thr Val Tyr
        655                 660                 665 aga ccc aca cta aca aaa gtc aaa att gaa ggt gaa cct gaa ttc aga   2066
Arg Pro Thr Leu Thr Lys Val Lys Ile Glu Gly Glu Pro Glu Phe Arg
670                 675                 680                 685 ctg att aaa gaa ggt gaa aca ata act gaa gtg atc cat gga gag cca   2114
Leu Ile Lys Glu Gly Glu Thr Ile Thr Glu Val Ile His Gly Glu Pro
                690                 695                 700 att att aaa aaa tac acc aaa atc att gat gga gtg cct gtg gaa ata   2162
Ile Ile Lys Lys Tyr Thr Lys Ile Ile Asp Gly Val Pro Val Glu Ile
                    705                 710                 715 act gaa aaa gag aca cga gaa gaa cga atc att aca ggt cct gaa ata   2210
Thr Glu Lys Glu Thr Arg Glu Glu Arg Ile Ile Thr Gly Pro Glu Ile
            720                 725                 730 aaa tac act agg att tct act gga ggt gga gaa aca gaa gaa act ctg   2258
Lys Tyr Thr Arg Ile Ser Thr Gly Gly Gly Glu Thr Glu Glu Thr Leu
```

```
                              735                 740                 745
aag aaa ttg tta caa gaa gaa gac aca ccc gtg agg aag ttg caa gcc       2306
Lys Lys Leu Leu Gln Glu Glu Asp Thr Pro Val Arg Lys Leu Gln Ala
750                 755                 760                 765 aac aaa aaa gtt caa gga tct aga aga cga tta agg gaa ggt cgt tct       2354
Asn Lys Lys Val Gln Gly Ser Arg Arg Arg Leu Arg Glu Gly Arg Ser
                770                 775                 780 cag tga                                                               2360
Gln

<210> SEQ ID NO 6
<211> LENGTH: 782
<212> TYPE: PRT
<213> ORGANISM: Homo sapiens

<400> SEQUENCE: 6

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
        50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
        130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
                180                 185                 190

Gly Leu Phe Ile Asn His Tyr Pro Asn Gly Val Val Thr Val Asn Cys
            195                 200                 205

Ala Arg Ile Ile His Gly Asn Gln Ile Ala Thr Asn Gly Val Val His
        210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
                260                 265                 270

Ala Pro Thr Asn Glu Ala Phe Glu Lys Leu Pro Arg Gly Val Leu Glu
            275                 280                 285

Arg Ile Met Gly Asp Lys Val Ala Ser Glu Ala Leu Met Lys Tyr His
        290                 295                 300

Ile Leu Asn Thr Leu Gln Cys Ser Glu Ser Ile Met Gly Gly Ala Val
305                 310                 315                 320
```

-continued

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Asp Ile Val
            340                 345                 350

Thr Asn Asn Gly Val Ile His Leu Ile Asp Gln Val Leu Ile Pro Asp
                355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
                435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
    515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
    595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Arg Pro Thr
            660                 665                 670

Leu Thr Lys Val Lys Ile Glu Gly Glu Pro Glu Phe Arg Leu Ile Lys
    675                 680                 685

Glu Gly Glu Thr Ile Thr Glu Val Ile His Gly Glu Pro Ile Ile Lys
690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
                725                 730                 735

Arg Ile Ser Thr Gly Gly Gly Glu Thr Glu Glu Thr Leu Lys Lys Leu

```
                      740                 745                 750
Leu Gln Glu Glu Asp Thr Pro Val Arg Lys Leu Gln Ala Asn Lys Lys
          755                 760                 765

Val Gln Gly Ser Arg Arg Leu Arg Glu Gly Arg Ser Gln
          770                 775                 780

<210> SEQ ID NO 7
<211> LENGTH: 20
<212> TYPE: PRT
<213> ORGANISM: Artificial sequence
<220> FEATURE:
<223> OTHER INFORMATION: Synthetic Construct

<400> SEQUENCE: 7

Cys Pro Val Arg Lys Leu Gln Ala Asn Lys Lys Val Gln Gly Ser Arg
1               5                   10                  15

Arg Arg Leu Arg
            20
```

METHOD FOR DETECTION OF IDIOPATHIC INTERSTITIAL PNEUMONIA

TECHNICAL FIELD

The present invention relates to a method for detecting idiopathic interstitial pneumonia, a method for screening for a preventive and/or therapeutic agent for idiopathic interstitial pneumonia, and a kit used for these methods.

BACKGROUND ART

Idiopathic interstitial pneumonia (IIP) is a cryptogenic disease characterized by the fibrosis of lung tissues. It is extremely difficult to predict the onset and progression of this disease.

According to histological classification, idiopathic interstitial pneumonia is classified into several types of disease, such as idiopathic pulmonary fibrosis (IPF) (or also referred to as usual interstitial pneumonia (UIP)) and nonspecific interstitial pneumonia (NSIP). IPF/UIP patients and NSIP patients account for 80% to 90% of all idiopathic interstitial pneumonia patients. NSIP is further classified into fibrotic NSIP and cellular NSIP. At present, there are no effective methods for a medical treatment of idiopathic interstitial pneumonia. Idiopathic interstitial pneumonia has a poor prognosis, and the median survival period of this disease is 2 to 4 years after the diagnosis of the disease. On the other hand, the prognosis of NSIP is better than those of IPF/UIP. Among others, the prognosis of cellular NSIP is much better than that of fibrotic NSIP. Thus, since the prognosis of patients with idiopathic interstitial pneumonia is different depending on the type of the disease, it is important to determine the type of idiopathic interstitial pneumonia in order to predict the prognosis of the patient with this disease.

The diagnosis of idiopathic interstitial pneumonia has been mainly made by radiography, an image diagnosis such as CT, a physiological pulmonary function test, etc. The definitive diagnosis has been made by a histological diagnosis involving the biopsy of lung tissues. However, the diagnostic accuracy of such image diagnosis is not as high as that of the histological diagnosis, and further, the image diagnosis requires high skilled, specialized diagnostic techniques. Furthermore, it is difficult for such image diagnosis to perform a quantitative diagnosis.

Under the aforementioned circumstances, it has been desired to develop a noninvasive diagnosis in addition to such an image diagnosis.

Document 1 describes that allergic disease is examined using the expression level of a periostin gene as an indicator.

Document 2 describes that periostin (osteoblast-specific factor 2) is generated in fibroblasts as a result of response to stimulation with IL-4 or IL-13, and that such periostin may be associated with the pulmonary fibrosis of patients with bronchial asthma.

(Documents)
1. WO2002/052006
2. G. Takayama et al., J Allergy Clin Immunol, vol. 118, 98-104, 2006

DISCLOSURE OF THE INVENTION

Under such circumstances, it has been desired to develop a method for detecting idiopathic interstitial pneumonia using a marker, and the like.

The present inventors have conducted intensive studies directed towards achieving the aforementioned object. As a result, the inventors have found that the expression level of a periostin gene or the amount of a periostin protein is high in biological samples derived from patients with idiopathic interstitial pneumonia, and that idiopathic interstitial pneumonia can be detected using periostin as a marker. Based on these findings, the inventors have completed the present invention.

Specifically, the present invention provides a method for detecting or diagnosing idiopathic interstitial pneumonia, a method for screening for a preventive and/or therapeutic agent for idiopathic interstitial pneumonia, and a kit used for these methods, as described below.

(1) A method for detecting or diagnosing idiopathic interstitial pneumonia, which comprises measuring the expression level of a periostin gene or the amount of a periostin protein in a biological sample.

(2) The method according to (1) above, wherein the idiopathic interstitial pneumonia is idiopathic pulmonary fibrosis or nonspecific interstitial pneumonia.

(3) The method according to (2) above, wherein the nonspecific interstitial pneumonia is fibrotic nonspecific interstitial pneumonia (fibrotic NSIP).

(4) The method according to any one of (1) to (3) above, wherein the measurement is carried out by an immunoassay.

(5) The method according to any one of (1) to (4) above, wherein the biological sample is lung tissues and/or blood.

(6) The method according to any one of (1) to (5) above, which comprises comparing (i) the expression level of a periostin gene or the amount of a periostin protein in a biological sample derived from a subject, with (ii) the expression level of a periostin gene or the amount of a periostin protein in normal cells.

(7) The method according to (6) above, which comprises determining that the subject has or is suspected to have idiopathic interstitial pneumonia, when (i) the expression level of a periostin gene or the amount of a periostin protein in the biological sample derived from the subject is higher than (ii) the expression level of a periostin gene or the amount of a periostin protein in the normal cells.

(8) A method for screening for a preventive and/or therapeutic agent for idiopathic interstitial pneumonia, which comprises measuring the expression level of a periostin gene or the amount of a periostin protein, in a case in which cells having ability to produce periostin have been cultured in the presence of a candidate substance.

(9) The method according to (8) above, wherein the idiopathic interstitial pneumonia is idiopathic pulmonary fibrosis or nonspecific interstitial pneumonia.

(10) The method according to (9) above, wherein the nonspecific interstitial pneumonia is fibrotic nonspecific interstitial pneumonia (fibrotic NSIP).

(11) The method according to any one of (8) to (10) above, wherein the measurement is carried out by an immunoassay.

(12) The method according to any one of (8) to (11) above, wherein the biological sample is lung tissues and/or blood.

(13) The method according to any one of (8) to (12) above, which comprises comparing (i) the expression level of a periostin gene or the amount of a periostin protein in a case in which cells having ability to produce periostin have been cultured in the presence of a candidate substance, with (ii) the expression level of a periostin gene or the amount of a periostin protein in a case in which cells having ability to produce periostin have been cultured in the absence of a candidate substance.

(14) The method according to (13) above, which comprises selecting a candidate substance, when (i) the expression level of a periostin gene or the amount of a periostin protein in a case in which cells having ability to produce periostin have been cultured in the presence of the candidate substance is lower than (ii) the expression level of a periostin gene or the amount of a periostin protein in a case in which cells having ability to produce periostin have been cultured in the absence of the candidate substance.

(15) A kit for detecting idiopathic interstitial pneumonia, which comprises a polynucleotide having the nucleotide sequence of a periostin gene, or a polynucleotide with a length of at least 21 nucleotides, which has a nucleotide sequence complementary to a complementary strand thereof

(16) A kit for detecting idiopathic interstitial pneumonia, which comprises an antibody that recognizes a peptide having the amino acid sequence of a periostin protein.

(16a) The kit according to (15) or (16) above, wherein the idiopathic interstitial pneumonia is idiopathic pulmonary fibrosis or nonspecific interstitial pneumonia.

(16b) The kit according to (16a) above, wherein the nonspecific interstitial pneumonia is fibrotic nonspecific interstitial pneumonia (fibrotic NSIP).

(17) A kit for screening for a preventive and/or therapeutic agent for idiopathic interstitial pneumonia, which comprises cells having ability to produce periostin.

(17a) The kit according to (17) above, wherein the idiopathic interstitial pneumonia is idiopathic pulmonary fibrosis or nonspecific interstitial pneumonia.

(17b) The kit according to (17a) above, wherein the nonspecific interstitial pneumonia is fibrotic nonspecific interstitial pneumonia (fibrotic NSIP).

According to the present invention, a method for detecting idiopathic interstitial pneumonia using a novel marker, and the like, are provided. In a preferred embodiment of the present invention, the invention is advantageous in that, for example, the detection results can be used to assist the definitive diagnosis of idiopathic interstitial pneumonia.

The patent or application file contains at least one color drawing. Copies of this patent or patent application publication with color drawing will be provided by the USPTO upon request and payment of the necessary fee.

BEST MODE FOR CARRYING OUT THE INVENTION

The present invention will be described in detail below.

It is to be noted that all publications cited in the present specification, which include prior art documents and patent documents such as laid-open application publications and patent publications, are incorporated herein by reference in their entirety. The present specification includes the contents as disclosed in the claims, specification and drawings of Japanese Patent Application No. 2008-147822, which is a priority document of the present application.

1. Summary of the Present Invention

The present invention relates to a method for detecting or diagnosing idiopathic interstitial pneumonia, which comprises measuring the expression level of a periostin gene or the amount of a periostin protein in a biological sample.

The present inventors have conducted intensive studies directed towards obtaining a marker that can be used for the detection of idiopathic interstitial pneumonia. As a result, the inventors have found that the expression level of a periostin gene or the amount of a periostin protein is high in the lung tissues, blood and the like of patients suffering from idiopathic interstitial pneumonia.

Specifically, the amount of a periostin protein in lung tissues derived from patients suffering from idiopathic interstitial pneumonia was measured by a histological staining method. As a result, the amount of a periostin protein was high in all of 23 IPF/UIP patients and 23 fibrotic NSIP patients (FIGS. 1(a) and 1(b)). The amount of a periostin protein was extremely low in 4 cellular NSIP patients (FIG. 1(c)). On the other hand, the amount of a periostin protein was extremely low in all of the normal lung tissues of 6 persons used as a control group (FIG. 1(d)).

Figure 2:
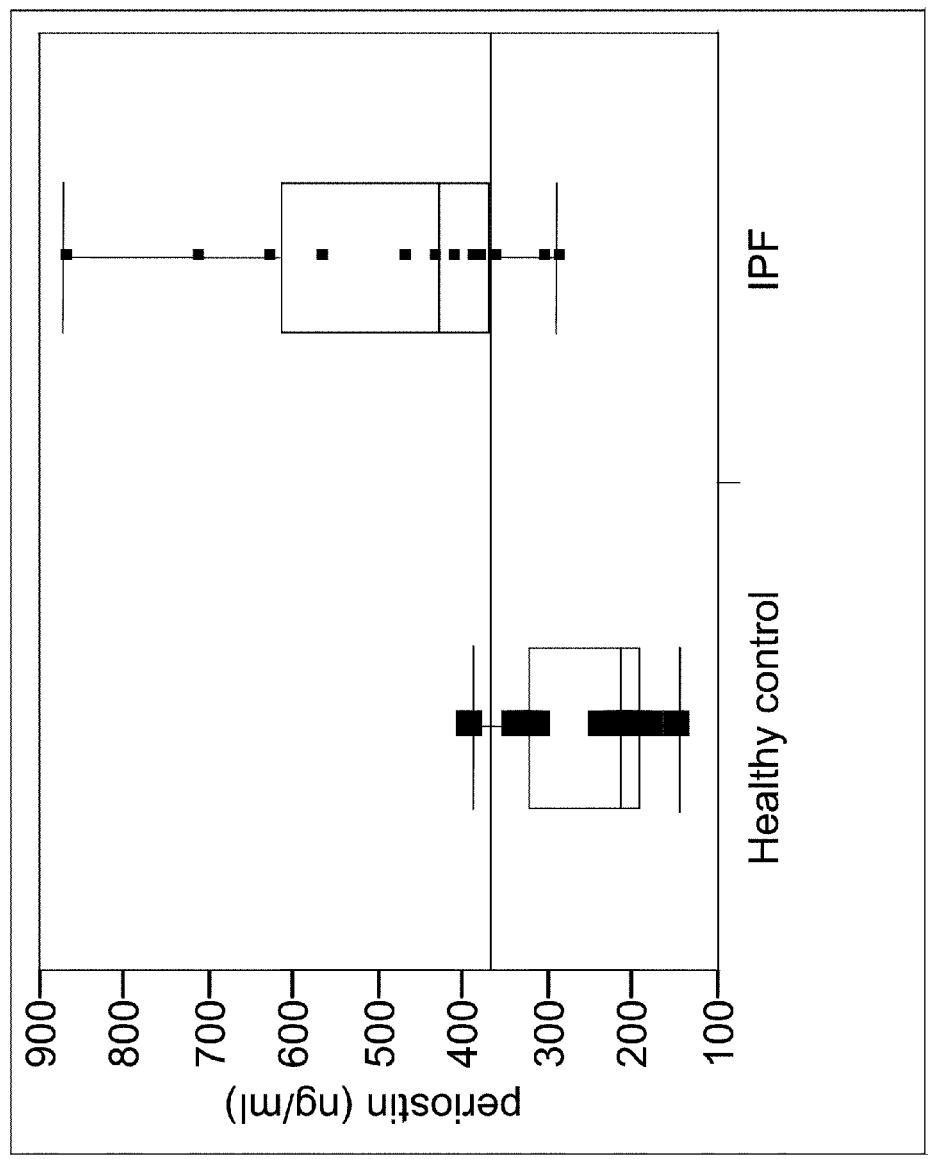
FIG. 2 is a graph showing the results obtained by the ELISA measurement of a blood periostin level.

Moreover, the amount of a periostin protein in blood collected from idiopathic interstitial pneumonia patients was measured by an immunoassay. A comparison was made between the results of 13 IPF/UIP patients and the results of 12 normal persons. As a result, it was found that there was a significant difference between the two groups and that the amount of a periostin protein was significantly increased in the blood of the IPF/UIP patients (FIG. 2).

As stated above, the expression level of a periostin gene or the amount of a periostin protein becomes high in tissues derived from patients with idiopathic interstitial pneumonia. Based on these results, the present inventors have found that periostin is useful as a marker for detecting idiopathic interstitial pneumonia.

Furthermore, the present invention also provides a method for screening for a preventive and/or therapeutic agent for idiopathic interstitial pneumonia, which comprises measuring the expression level of a periostin gene or the amount of a periostin protein, in a case in which cells having ability to produce periostin have been cultured in the presence of a candidate substance.

As described above, the expression level of a periostin gene is increased in tissues derived from patients with idiopathic interstitial pneumonia, and the periostin protein level becomes high in tissues derived from the patients. Accordingly, a compound that decreases the expression level of the periostin gene or the amount of the periostin protein when it is administered to the patient, or a salt thereof; namely, a compound that inhibits the aforementioned expression, or a salt thereof (e.g. a peptide, a protein, a synthetic compound, an anti-periostin antibody, or a salt thereof), can be used as a preventive and/or therapeutic agent for idiopathic interstitial pneumonia.

Further, the present invention also provides a kit used for the above-described method for detecting or diagnosing idiopathic interstitial pneumonia or the above-described method for screening for a preventive and/or therapeutic agent for idiopathic interstitial pneumonia.

2. Periostin

Periostin is an approximately 90 kDa protein, which is also referred to as "osteoblast-specific factor 2" (OSF2os; Horiuchi K, Amizuka N, Takeshita S, Takamatsu H, Katsuura M, Ozawa H, Toyama Y, Bonewald L F, Kudo A.; Identification and characterization of a novel protein, periostin, with restricted expression to periosteum and periodontal ligament and increased expression by transforming growth factor beta.

J Bone Miner Res. July 1999; 14(7): 1239-49.). It has been known that periostin has several transcripts, which can be distinguished from one another in terms of the length on the C-terminal side caused by alternative splicing. Herein, the DNA sequence of a transcript containing all exons of a human periostin gene is shown in SEQ ID NO: 1 (Accession No. D13666). In addition, examples of the DNA sequences of other splicing variants of human periostin are shown in SEQ ID NOS: 3 and 5 (Accession Nos. AY918092 and AY140646, respectively). Moreover, the amino acid sequences of periostins are shown respectively in SEQ ID NOS: 2,4 and 6 which are encoded by the corresponding polynucleotides shown in SEQ ID NOS: 1, 3 and 5.

In a preferred embodiment of the present invention, the expression level of a periostin gene or the amount of a periostin protein, which contains a variant derived from the amino acid sequence shown in SEQ ID NO: 2 (for example, periostin consisting of the amino acid sequence shown in SEQ ID NO: 2, 4, or 6), is measured.

3. The Method of the Present Invention for Detecting or Diagnosing Idiopathic Interstitial Pneumonia The expression level of a periostin gene or the amount of a periostin protein is increased in tissues derived from a patient with idiopathic interstitial pneumonia. Thus, periostin in a biological sample derived from a subject can be used as a marker for detecting or diagnosing idiopathic interstitial pneumonia. Specifically, the present invention provides a method for detecting idiopathic interstitial pneumonia, which comprises measuring the expression level of a periostin gene or the amount of a periostin protein in a biological sample. More specifically, (i) the expression level of a periostin gene or the amount of a periostin protein in a biological sample derived from a subject is compared with (ii) the expression level of a periostin gene or the amount of a periostin protein in normal cells, for example. That is, the amount of a periostin protein or the level of mRNA encoding periostin is measured, and the obtained values are then compared. Examples of a biological sample that can be used for the measurement of the expression level or the protein amount include lung tissues, blood, sputum, an exhaled breath condensate and a bronchoalveolar lavage fluid, which are derived from a subject, and a bronchial lining fluid collected using a bronchoscope. Preferably, a subject-derived lung tissue or blood is used. Methods for collecting lung tissues, blood, sputum, an exhaled breath condensate and a bronchoalveolar lavage fluid, and a method for collecting a bronchial lining fluid using a bronchoscope, are known. Normal cells mean cells derived from a person who is not affected with idiopathic interstitial pneumonia, for example. When the biological sample is lung tissue, sputum or like, it is preferable, for example, to prepare a lysate from the biological sample, or to extract mRNA from the biological sample, in order to use it for the measurement of the expression level or the protein amount. Preparation of a lysate and extraction of mRNA can be carried out by known methods, and commercially available kits are used, for example. When the biological sample is a liquid sample such as blood or a bronchoalveolar lavage fluid, it is diluted with a buffer or the like, and it is then preferably used to measure the level of mRNA encoding periostin, for example. The amount of a periostin protein can be measured by, for example, an immunoassay or the like. Preferably, the amount of a periostin protein can be measured by an immunoassay. Examples of such an immunoassay include a radioimmunoassay (RIA), a fluorescent immunoassay (FIA), a luminescent immunoassay, an enzyme immunoassay (e.g. Enzyme Immunoassay (EIA) and Enzyme-linked Immunosorbent assay (ELISA)), and a Western blot method. Examples of a radioactive substance that can be used for labeling in RIA include $^{125}I$, $^{131}I$, $^{14}C$, $^{3}H$, $^{35}S$ and $^{32}P$. Examples of a fluorescent substance that can be used for labeling in FIA include fluorescent substances such as Eu (europium), FITC, TMRITC, Cy3, PE and Texas-Red. Examples of a luminescent substance that can be used for labeling in a luminescent immunoassay include luminol, luminol derivatives, luciferin and lucigenin. Examples of an enzyme that can be used for labeling in an enzyme immunoassay include horseradish peroxidase (HRP), alkaline phosphatase (ALP) and glucose oxidase (GO). Furthermore, a biotin-avidin system can also be used for the binding of an antibody or an antigen with these labeling substances. The measurement of an amount of mRNA can be carried out by a known method, for example, using a polynucleotide having the nucleotide sequence of a periostin gene or a portion thereof. More specifically, for example, the measurement can be carried out using a DNA chip, on which a polynucleotide having the nucleotide sequence shown in SEQ ID NO: 1, 3 or 5, or a portion thereof, has been immobilized; using Northern hybridization in which a polynucleotide having the nucleotide sequence shown in SEQ ID NO: 1, 3 or 5, or a portion thereof, is used as a probe; or using a PCR method in which a polynucleotide having the nucleotide sequence shown in SEQ ID NO: 1, 3 or 5, or a portion thereof, is used as a primer. For example, when the expression level of a periostin gene or the amount of a periostin protein in the above case (i) is higher than the expression level of a periostin gene or the amount of a periostin protein in the above case (ii); namely, when the expression level of a periostin gene or the amount of a periostin protein in the above ease (i) is higher than the expression level of a periostin gene or the amount of a periostin protein in the above case (ii), for example, by approximately 20% or more, approximately 30% or more, approximately 40% or more, approximately 50% or more, approximately 60% or more, approximately 70% or more, approximately 80% or more, approximately 90% or more, approximately 95% or more, or approximately 100% or more, it can be determined that the subject is suspected to have idiopathic interstitial pneumonia. The disease type of idiopathic interstitial pneumonia that can be detected by the above-described method is, for example, idiopathic pulmonary fibrosis/usual interstitial pneumonia (IPF/UIP), or nonspecific interstitial pneumonia (NSIP). Specifically, it is IPF/UIP or fibrotic NSIP.

Otherwise, the expression level of a periostin gene or the amount of a periostin protein may also be measured by immunohistochemistry. More specifically, (i) the expression level of a periostin gene or the amount of a periostin protein in a biological sample derived from a subject is compared with (ii) the expression level of a periostin gene or the amount of a periostin protein in normal cells, for example. That is to say, periostin or mRNA encoding such periostin is visualized by immunohistochemistry, and the amounts of periostin proteins or the mRNA levels of both cases are then compared. As a biological sample, lung tissues and the like can be used. Specific examples of immunohistochemistry include an enzyme-labeled antibody method and a fluorescent antibody method. Examples of the enzyme-labeled antibody method include: labeled antibody methods such as a direct method, an indirect method, an avidin-biotinylated peroxidase complex method (ABC method) or a streptavidin biotinylated antibody method (SAB method); and unlabeled antibody methods such as a peroxidase-antiperoxidase method (PAP method). The fluorescent antibody method includes a direct method and an indirect method. Enzymes or fluorescent substances used for labeling are the same as those described above. For example, when the expression level of a periostin gene or the amount of a periostin protein in the above case (i)

is higher than the expression level of a periostin gene or the amount of a periostin protein in the above case (ii); namely, when the expression level of a periostin gene or the amount of a periostin protein in the above case (i) is higher than the expression level of a periostin gene or the amount of a periostin protein in the above case (ii), for example, by approximately 20% or more, approximately 30% or more, approximately 40% or more, approximately 50% or more, approximately 60% or more, approximately 70% or more, approximately 80% or more, approximately 90% or more, approximately 95% or more, or approximately 100% or more, it can be determined that the subject is suspected to have idiopathic interstitial pneumonia. The disease type of idiopathic interstitial pneumonia that can be detected by the above-described method is, for example, idiopathic pulmonary fibrosis/usual interstitial pneumonia (IPF/UIP), or nonspecific interstitial pneumonia (NSIP). Specifically, it is IPF/UIP or fibrotic NSIP.

Herein, the difference between (i) the expression level of a periostin gene or the amount of a periostin protein in a biological sample derived from a subject and (ii) the expression level of a periostin gene or the amount of a periostin protein in normal cells is used as a critical value in the detection or diagnosis of idiopathic interstitial pneumonia. Such a critical value may be set as follows, for example. First, the expression levels of periostin genes or the amounts of periostin proteins in biological samples derived from two or more patients with idiopathic interstitial pneumonia (for example, IPF/UIP or fibrotic NSIP) are measured, and an average (A) is then obtained. In this operation, the number of target patients is two or more, and it is, for example, 5 or more, 10 or more, 50 or more, or 100 or more. On the other hand, the expression levels of periostin genes or the amounts of periostin proteins in cells derived from two or more normal persons are measured, and an average (B) is then obtained. In this operation, the number of target normal persons is two or more, and it is, for example, 5 or more, 10 or more, 50 or more, or 100 or more. Thereafter, [(A−B)/B]×100(%) is calculated using the obtained averages (A) and (B). The average of the expression levels of periostin genes or the amounts of periostin proteins in the biological samples derived from the patients with idiopathic interstitial pneumonia is compared with the average of the expression levels of periostin genes or the amounts of periostin proteins in the cells derived from the normal persons, and the percentage by which the former average is higher than the latter average is then determined. The thus determined value is defined as the difference (critical value) between (i) the expression levels of periostin genes or the amounts of periostin proteins in the biological samples derived from the subjects and (ii) the expression levels of periostin genes or the amounts of periostin proteins in the normal cells. That is, when the expression level of a periostin gene or the amount of a periostin protein in the above case (i) is higher than the difference obtained by comparing it with the expression level of a periostin gene or the amount of a periostin protein in the above case (ii) (for example, when it is statistically significantly high), it can be determined that the subject has or is suspected to have idiopathic interstitial pneumonia. In the method of the present invention for detecting or diagnosing idiopathic interstitial pneumonia, the expression level of a periostin gene or the amount of a periostin protein in a biological sample is measured. Thus, it is preferable to integrate measurement values into the averages (A) and (B), so that the number of target patients and the number of normal persons can increase. By increasing the number of cases, the accuracy of detection or diagnosis of idiopathic interstitial pneumonia can be enhanced. Moreover, the obtained average (B) of the expression levels of periostin genes or the amounts of periostin proteins in cells derived from normal persons may also be defined as "(ii) the expression level of a periostin gene or the amount of a periostin protein in normal cells."

The aforementioned detection results or diagnostic results of idiopathic interstitial pneumonia can be used, for example, as auxiliary information in making the definitive diagnosis of idiopathic interstitial pneumonia. When the definitive diagnosis of idiopathic interstitial pneumonia is made, the aforementioned detection results may be combined with at least one selected from the group consisting of the results of physical findings, serological examination results (for example, serum KL-6, LDH or SC-A levels, etc.), respiratory function test results, the results of chest X-ray image findings, and the results of chest HRCT image findings, so that the definitive diagnosis may be comprehensively made.

4. The Kit of the Present Invention for Detecting or Diagnosing Idiopathic Interstitial Pneumonia The present invention provides a kit that can be used for the above-described method for detecting or diagnosing idiopathic interstitial pneumonia.

In one embodiment of the present invention, the aforementioned kit comprises a polynucleotide having the nucleotide sequence of a periostin gene (for example, the nucleotide sequence shown in SEQ ID NO: 1, 3, or 5) or a portion thereof. Preferably, the aforementioned kit comprises a polynucleotide having the nucleotide sequence of a periostin gene, or a polynucleotide with a length of at least 21 nucleotides, which has a nucleotide sequence complementary to a complementary strand thereof. More preferably, the aforementioned kit may comprise the above-described polynucleotide, which is immobilized on a DNA chip.

In another embodiment of the present invention, the aforementioned kit comprises an antibody, which recognizes, and more preferably, specifically recognizes a peptide having the amino acid sequence of a periostin protein (for example, the amino acid sequence shown in SEQ ID NO: 2, 4 or 6). The aforementioned antibody may be either a monoclonal antibody or a polyclonal antibody. Thus, the type of the antibody is not limited. The antibody can be produced by a method well known in the present technical field.

As a method for producing an antibody, when the antibody to be produced is a polyclonal antibody, for example, an antigen, together with an adjuvant, is administered to a mammal such as a rabbit to carry out immunization for a predetermined period of time, so that an antiserum is obtained. For the measurement of an antibody titer, an ordinary enzyme immunoassay (an ELISA method or an EIA method) and the like can be adopted.

On the other hand, when a monoclonal antibody is produced, immunocompetent cells (splenic cells, etc.) collected from an animal immunized with an antigen are fused with myeloma cells, and the thus fused cells are then screened in a selective medium such as an HAT medium, so that a hybridoma producing an antibody of interest is obtained. This hybridoma is cultured, so that a monoclonal antibody of interest is obtained.

The aforementioned antibody may be labeled with a radioactive substance, a fluorescent substance, an enzyme, and the like. Moreover, the aforementioned kit may comprise a labeled secondary antibody.

The aforementioned kit may comprise a container and a label, as well as the above-described items. The label placed on or included with the container may describe that the kit is used for the detection or diagnosis of idiopathic interstitial pneumonia. Moreover, the kit may further comprise other items such as instructions for use.

5. The Screening Method of the Present Invention

The expression of a periostin gene is increased in tissues derived from a patient with idiopathic interstitial pneumonia. Thus, a compound that decreases the expression level of the periostin gene or the amount of the periostin protein when it is administered to the patient, or a salt thereof; namely, a compound that inhibits the aforementioned expression or a salt thereof can be used as a preventive and/or therapeutic agent for idiopathic interstitial pneumonia. That is to say, the present invention provides a method for screening for a compound that decreases the expression level of a periostin gene or the amount of a periostin protein, or a salt thereof, wherein the method comprises measuring the expression level of a periostin gene or the amount of a periostin protein, in a case in which cells having ability to produce periostin have been cultured in the presence of a candidate substance. More specifically, (i) a case in which cells having ability to produce periostin have been cultured in the presence of a candidate substance is compared with (ii) a case in which cells having ability to produce periostin have been cultured in the absence of a candidate substance, in terms of the expression level of a periostin gene or the amount of a periostin protein, for example. For the comparison, for example, the expression level of a periostin gene or the amount of a periostin protein is measured in both cases (i) and (ii), and the result of the case (i) is then compared with the result of the case (ii). Specifically, the amount of a periostin protein or the level of mRNA encoding periostin is measured in both cases (i) and (ii), and the result of the case (i) is then compared with the result of the case (ii). The cells having ability to produce periostin are, for example, cells transformed with a vector containing DNA encoding periostin. Examples of cells to be transformed include CHO cells, HEK293 cells, and 293 cells. The transformed cells may be cultured by a known method. Examples of the above-described candidate substance include a peptide, a protein, a synthetic compound, and a salt thereof. The amount of a periostin protein may be measured by the above-described immunoassay or a protein chip method, for example. The level of mRNA may be measured by a known method, such as a method using a polynucleotide having the nucleotide sequence of a periostin gene or a portion thereof. More specifically, for example, the measurement can be carried out using a DNA chip, on which a polynucleotide having the nucleotide sequence shown in SEQ ID NO: 1, 3 or 5, or a portion thereof, has been immobilized; using Northern hybridization in which a polynucleotide having the nucleotide sequence shown in SEQ ID NO: 1, 3 or 5, or a portion thereof, is used as a probe; or using a PCR method in which a polynucleotide having the nucleotide sequence shown in SEQ ID NO: 1, 3 or 5, or a portion thereof, is used as a primer. After completion of the measurement, for example, a candidate substance, which decreases the expression level of periostin or the amount of a periostin protein in the above case (i) when compared with that in the above case (ii); namely, a candidate substance, which decreases the expression level of periostin or the amount of a periostin protein in the above case (i), for example, by approximately 20% or more, approximately 30% or more, approximately 40% or more, approximately 50% or more, approximately 60% or more, approximately 70% or more, approximately 80% or more, approximately 90% or more, approximately 95% or more, or approximately 100% or more, when compared with that in the above case (ii), can be selected as a compound that inhibits the expression of a periostin gene, or a salt thereof.

6. The Screening Kit of the Present Invention

The present invention provides a kit that can be used for the above-described method for screening for a preventive and/or therapeutic agent for idiopathic interstitial pneumonia. Specifically, the aforementioned kit comprises cells having ability to produce periostin. The "cells having ability to produce periostin" are as described above in the screening method of the present invention. The aforementioned kit may further comprise a medium used for cell culture, an antibiotic and a serum (a fetal bovine serum, etc.), which are to be added to the medium, and the like.

In addition, the kit may comprise a component used to measure the expression level of a periostin gene or the amount of a periostin protein. Examples of such a component include a polynucleotide having the nucleotide sequence of a periostin gene or a portion thereof, and an antibody that recognizes a peptide having the amino acid sequence of a periostin protein. These polynucleotide and antibody are the same as those described above.

The aforementioned kit may comprise a container and a label, as well as the above-described items. The label placed on or included with the container may describe that the kit is used to screen for a preventive and/or therapeutic agent for idiopathic interstitial pneumonia. Moreover, the kit may further comprise other items such as instructions for use.

Hereinafter, the present invention will be further specifically described in the following examples. However, these examples arc not intended to limit the scope of the present invention.

EXAMPLES (1) Production of Rabbit Polyclonal Anti-periostin Antibody

A recombinant protein formed by adding V5 epitope/His tag to periostin (nucleotide sequence: SEQ ID NO: 1, Accession No. D13666; amino acid sequence: SEQ ID NO: 2, Accession No. BAA02837) was expressed in S2 cells as insect cells, and it was then purified.

Specifically, transformants of S2 cells were produced as follows. cDNA encoding the above-described portion of periostin was inserted into a pMT/Bip/V5-HisA plasmid to produce pMT/Bip/V5-HisA-periostin. The pMT/Bip/V5-HisA-periostin and pCoHygro (Invitrogen) used as a plasmid for the expression of a hygromycin resistance gene were co-introduced into S2 cells according to a known method, so that the cells were transformed. Thereafter, transformants were selected using hygromycin, so that stable transformants were obtained.

Subsequently, V5 epitope/His tag-bound periostin was expressed in the transformants of the S2 cells.

The recombinant protein was purified as follows. Cupric sulfate was added to a medium comprising the stable transformants of the S2 cells containing periostin genes, so that the expression of the recombinant protein is induced. Thereby, the recombinant protein was expressed and secreted into a culture supernatant. This culture supernatant was dialyzed against PBS, and it was then mixed with a nickel resin (Ni-NTA Agarose, Qiagen, Hilden, Germany), so that the recombinant protein was allowed to bind to the resin. The resin was washed to remove contaminants, and the recombinant protein was then eluted with an imidazole-containing buffer. The eluted recombinant protein was dialyzed against PBS, and the resultant was used as an immunogen for animals.

Subsequently, such a recombinant protein was mixed with CFA (a complete Freund's adjuvant) (Freund's Adjuvant, Complete, manufactured by Sigma). A rabbit was immunized with the mixture, and serum was then collected from the rabbit.

Specific procedures are as follows. New Zealand White rabbits (female; body weight: 1.5-2 kg; KBT Oriental Co., Ltd., Tosu, Japan) were used.

These rabbits were immunized by injecting a mixture of recombinant periostin used as an immunogen and CFA into several sites in the dorsal subcutis of each rabbit.

Five to seven weeks after the immunization, blood was collected from the ear vein of each immunized rabbit, and serum was then obtained.

Finally, IgG was purified from the serum as follows. That is, to the collected serum, 50 mM sodium acetate (pH 4.0) was added in two times the amount of the serum. Thereafter, the pH of the obtained solution was adjusted to pH 4.0 by the addition of hydrochloric acid. While stirring the serum, caprylic acid was added thereto in an amount of $\frac{1}{15}$ of the serum. The obtained mixture was stirred for 30 minutes, and was then centrifuged at 9200 g for 10 minutes. The supernatant was dialyzed against PBS, so that purified IgG was prepared.

(2) Production of Rat Monoclonal Anti-periostin Antibody

A KLII (keyhole limpet hemocyanin)-bound human periostin peptide (20-50 μg/rat) or an S2 recombinant periostin protein (20-50 μg/rat) was mixed with CFA (a complete Freund's adjuvant) or TiterMax Gold (a chemically synthesized adjuvant), and the thus obtained binding form was used as an immunogen.

Specific procedures are as follows. The Sigma company was asked to produce a KLH-bound human periostin peptide by binding KLH having a maleimide group to a periostin peptide (CPVRKLQANKKVQGSRRRLR; SEQ ID NO: 7) produced by an Fmoc method.

Subsequently, an S2 recombinant periostin protein was produced as follows. First, cupric sulfate was added to a medium comprising the stable transformants of the S2 cells containing periostin genes, so that the expression of the recombinant periostin protein was induced. Thereby, the recombinant periostin protein was expressed and secreted into a culture supernatant. This culture supernatant was dialyzed against PBS, and it was then mixed with a nickel resin (Ni-NTA Agarose, Qiagen, Hilden, Germany), so that the recombinant periostin was allowed to bind to the resin. The resin was washed to remove contaminants, and the S2 recombinant periostin protein was then eluted with an imidazole-containing buffer.

As CFA, there was used Freund's Adjuvant, Complete, manufactured by Sigma. TiterMax Gold was purchased from Funakoshi Co., Ltd. CFA or TiterMax Gold was mixed at a volume ratio of 1:1 with a KLH-bound human periostin peptide solution or an S2 recombinant periostin protein solution.

Subsequently, 20-50 μg of the mixture of the KLH-bound human periostin peptide solution or S2 recombinant periostin protein solution and CFA or TiterMax Gold, which was used as an immunogen, was injected into the subcutis of the foot pad of a female rat. Ten days to two weeks later, 20-50 μg of the mixture of the KLH-bound human periostin peptide solution or S2 recombinant periostin protein solution and CFA or TiterMax Gold, used as an immunogen, was injected again into the subcutis of the foot pad of the female rat. In this experiment, a 6 to 8-week-old female Wistar rat (Charles River Laboratories Japan, Inc., Yokohama, Japan) was used.

Three to four days after the final immunization, cells in the popliteal, inguinal, and iliac lymph nodes of the immunized rat, were mixed with myeloma cells at a mixing ratio of 1:1 to 10:1, and polyethylene glycol was then added to the mixed cells according to an ordinary method, so that cell fusion was carried out. Thereafter, hybridoma colonies were selected.

Specifically, cell fusion was carried out as follows. The mixed lymph node cells and myeloma cells were centrifuged, and a supernatant was then removed. The residue was suspended in 1 ml of polyethylene glycol (PEG1500, Roche, Switzerland) at room temperature over 1 minute, and the suspension was then stirred at 37° C. for 1 minute. 1 ml of a serum-free medium was added to the reaction solution over 1 minute, and 10 ml of a serum-free medium was then added thereto over 1 minute. The cells were washed several times, and they were then dispensed in a 96-well plate, followed by performing culture at 37° C. in the presence of 5% $CO_2$.

As a method of selecting hybridoma cells, 7 to 14 days after the cell fusion, the peptide or protein used as an antigen was solid-phased, and selection of the hybridoma cells was then carried out in an ELISA system, in which the fused cell culture supernatant was used as a primary antibody. ELISA was specifically carried out as follows. The 1 μg/ml peptide or protein was dispensed in a 96-well plate, and was then solid-phased for several hours. The solid-phased solution was washed, and the fused cell culture supernatant was then added to each well, followed by leaving it at rest at room temperature for 1 hour. Thereafter, the fused cell culture supernatant was washed, and a peroxidase-labeled goat anti-rat IgG antibody (GE Healthcare, Little Chalfont, U.K.) used as a secondary antibody was added thereto, followed by leaving it at rest at room temperature for 1 hour. After the secondary antibody had been washed, an ABTS peroxidase substrate (KPL, Gaithersburg, Md.) was added thereto for color development. Then, the absorbance at 405 nm was measured.

Thereafter, IgG was purified from the selected hybridoma cells as follows. The hybridoma cells were injected into the abdominal cavity of a 6 to 8-week-old female ICR-SCID mouse (CLEA Japan, Inc., Tokyo, Japan). Seven to ten days after the injection, accumulated ascites was collected. To the collected ascites, 50 mM sodium acetate (pH 4.0) was added in two times the amount of the ascites. Thereafter, the pH of the obtained solution was adjusted to pH 4.0 by the addition of hydrochloric acid. While stirring the serum, caprylic acid was added thereto in an amount of $\frac{1}{15}$ of the serum. The obtained mixture was stirred for 30 minutes, and was then centrifuged at 9200 g for 10 minutes. The supernatant was dialyzed against PBS, so that purified IgG was obtained.

(3) ELISA Measurement of Blood Periostin Level

A rabbit polyclonal anti-periostin antibody was solid-phased on a plate, and a standard substance or a biological sample (sample) was then added thereto.

Specifically, solid-phase preparation was carried out as follows. A 10 μg/ml unlabeled rabbit polyclonal anti-periostin antibody was dispensed in a 96-well plate, and it was then solid-phased at 4° C. overnight.

An S2 recombinant periostin protein was used as a standard substance, and it was added at a concentration of 0-1000 ng/ml in an amount of 50 μl/well. As samples, blood collected from 13 IPF/UIP patients and blood collected from 12 normal persons were used. Such blood was collected from the peripheral vein, using a vacuum blood collecting tube, without the addition of heparin (plain). The collected blood was dispensed in tubes (1 ml per tube), and was then preserved at -30° C. The frozen blood samples were thawed before measurement, and serum was then recovered from the thawed blood by centrifugation. The serum was diluted by a factor of 10, and it was then added to the plate in an amount of 50μl/well.

Thereafter, a biotin-labeled rabbit polyclonal anti-periostin antibody (1 μg/ml) used as a primary antibody was also added to the plate in an amount of 50 μl/well, and then, 50 μl/well Eu (europium)-labeled streptavidin or 50 μl/well HRP-labeled streptavidin was further added thereto. Subsequently, fluorescence or color developed was measured using a plate reader (ARVO MX, manufactured by Perkin Elmer). The measurement values of the samples were applied to a standard curve, which had been produced based on the measurement values of the standard substance, followed by calculation, so that the amount of periostin (ng/ml) contained in each sample was obtained.

The results are shown in FIG. 2. As shown in FIG. 2, the amount of periostin in the biological sample (IPF) derived from IPF/UIP patients was larger than that in the biological sample (Healthy Control) derived from normal persons (with a significant difference, $p<0.001$). Moreover, when a comparison was made between the two types of biological samples in terms of mean value, the amount of a periostin protein in the biological sample (IPF/UIP) derived from the IPF/UIP patients was larger than that in the biological sample (Healthy Control) derived from the normal persons by approximately 95% ([(the mean value of IPF periostin amount−the mean value of Healthy Control periostin amount)/the mean value of Healthy Control periostin amount]×100(%)=[(491−252)/252]×100(%)).

(4) Histoimmunostaining of Periostin

Periostin was histoimmunostained according to a histoimmunostaining method, which is generally referred to as an "ABC method."

Paraffin-embedded lung tissues were used as biological samples. Such paraffin-embedded lung tissues were produced by collecting lung tissues from each of 23 IPF/UIP patients, 23 fibrotic NSIP patients, 4 cellular NSIP patients and 6 normal persons, and then embedding the collected lung tissues in paraffin. The thus produced lung tissues were subjected to treatments such as deparaffinization, inhibition of endogenous peroxidase activity and blocking Specifically, these operations were carried out as follows. The tissues were treated with methanol+3% $H_2O_2$ for 15 to 30 minutes, and were then treated with Protein Block Serum-Free (DAKO, Glostrup, Denmark) for 5 to 10 minutes.

The rabbit polyclonal anti-periostin antiserum or rat monoclonal anti-periostin antibody as produced above was used as a primary antibody, and it was added to the tissues in a dilution factor of 1000 or in a concentration of 10 μg/ml. Thereafter, an HRP-labeled antibody (Envision, purchased from DAKO) directed against the primary antibody was added as a secondary antibody, and color was then developed with DAB (diaminobenzidine) (Sigma).

Thereafter, operations such as nuclear staining, dehydration and mounting were carried out. Specifically, these operations were carried out as follows. 100 μl of the primary antibody was placed on the tissues, and it was then left at rest at room temperature for 60 minutes. The primary antibody was then washed. Thereafter, 100 μl of the secondary antibody was placed on the tissues, and it was then left at rest at room temperature for 60 minutes. The secondary antibody was then washed. Subsequently, the tissue slide was immersed in a DAB substrate solution, so that color was developed for 1 to 20 minutes. Thereafter, the resultant was subjected to nuclear staining with hematoxylin, and was then subjected to dehydration and mounting according to known methods.

Figure 1:
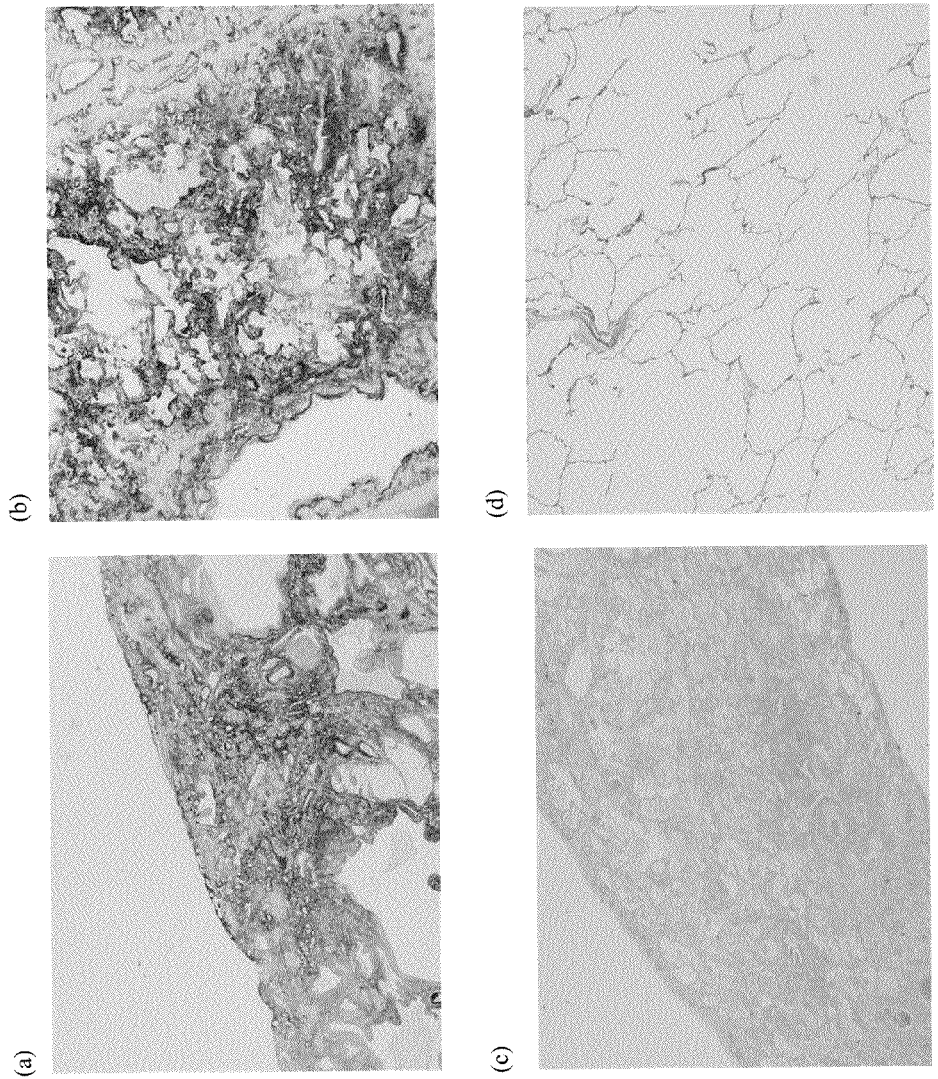
FIG. 1 includes photographs showing the results obtained by histoimmunostaining of periostin in lung tissues. (a) IPF/UIP, (b) fibrotic NSIP, (c) cellular NSIP, and (d) a healthy control.

As a result, it was found that the expression level of a periostin gene was high in all of the 23 IPF/UIP patients and the 23 fibrotic NSIP patients (FIGS. 1(a) and (b)). The expression level of a periostin gene was extremely low in the 4 cellular NSIP patients (FIG. 1(c)). In contrast, the expression level of a periostin gene was extremely low in all of the lung tissues from the 6 normal persons who constituted a control group (FIG. 1(d)).

As described in the above examples, since the expression of a periostin gene is increased in tissues derived from a patient with idiopathic interstitial pneumonia, periostin in a biological sample derived from a subject can be used as a marker for detecting or diagnosing idiopathic interstitial pneumonia.

Moreover, since the expression of the periostin gene is increased in tissues derived from a patient with idiopathic interstitial pneumonia, a compound that inhibits the expression of the periostin gene or a salt thereof can be used as a preventive and/or therapeutic agent for idiopathic interstitial pneumonia.

[Sequence Listing Free Text]

SEQ ID NO: 7 Synthetic structure

The invention claimed is:

1. A method for detecting idiopathic interstitial pneumonia, which comprises:
   a) obtaining a biological sample from a subject suspected of having idiopathic interstitial pneumonia; and
   b) measuring the expression level of a periostin gene or the amount of a periostin protein in a biological sample obtained from the subject suspected of having idiopathic interstitial pneumonia,
   wherein the periostin gene is selected from the group consisting of polynucleotide sequences set forth in SEQ ID NOs: 1, 3 and 5, and wherein the periostin protein is selected from the group consisting of amino acid sequences set forth in SEQ ID NOs: 2, 4 and 6, and
   wherein an elevated expression level of the periostin gene or an elevated amount of the periostin protein is indicative of idiopathic interstitial pneumonia,
   wherein the subject is suspected of having idiopathic interstitial pneumonia by having tested positive for idiopathic interstitial pneumonia with at least one selected from the group consisting of the results of physical findings, serological examination results, respiratory function test results, the results of chest X-ray image findings, and the results of chest HRCT image findings.

2. The method according to claim 1, wherein the idiopathic interstitial pneumonia is idiopathic pulmonary fibrosis or nonspecific interstitial pneumonia.

3. The method according to claim 2, wherein the nonspecific interstitial pneumonia is fibrotic nonspecific interstitial pneumonia (fibrotic NSIP).

4. The method according to claim 1, wherein the measurement is carried out by an immunoassay.

5. The method according to claim 1, wherein the biological sample is lung tissues and/or blood.

6. The method according to claim 1, which comprises comparing (i) the expression level of a periostin gene or the amount of a periostin protein in a biological sample derived from a subject, with (ii) the expression level of a periostin gene or the amount of a periostin protein in a biological sample derived from a normal person.

7. The method according to claim 6, which comprises determining that the subject has or is suspected to have idiopathic interstitial pneumonia, when (i) the expression level of a periostin gene or the amount of a periostin protein in the biological sample derived from the subject is higher than (ii) the expression level of a periostin gene or the amount of a periostin protein in the biological sample derived from a normal person.

8. The method according to claim 1, wherein the periostin gene is the polynucleotide sequence set forth in SEQ ID NO: 1, and wherein the periostin protein is the amino acid sequence set forth in SEQ ID NO: 2.

* * * * *